United States Patent [19]
Rodriguez

[11] Patent Number: 5,411,493
[45] Date of Patent: May 2, 1995

[54] SPONGE BATH GARMENT AND METHOD FOR USING

[76] Inventor: Victorio C. Rodriguez, 7791 Hoertz Rd., Parma, Ohio 44134

[21] Appl. No.: 126,928

[22] Filed: Sep. 27, 1993

[51] Int. Cl.⁶ ............................................. A61M 35/00
[52] U.S. Cl. .................................. 604/290; 604/304; 2/97; 2/102
[58] Field of Search ................. 607/81, 83–87, 607/104; 604/289, 290, 291, 304, 305; 62/259.3; 165/46; 2/81, 197, 102, 108

[56] References Cited

U.S. PATENT DOCUMENTS

| | | | |
|---|---|---|---|
| 546,436 | 9/1895 | Springsteen | 165/46 X |
| 3,195,539 | 7/1965 | Hyman | 607/83 X |
| 3,452,554 | 7/1969 | Smith | 62/259.3 |
| 3,610,323 | 10/1971 | Troyer | 165/46 |
| 3,867,939 | 2/1975 | Moore et al. | 607/104 X |
| 4,114,620 | 9/1978 | Moore et al. | 607/104 |
| 4,580,408 | 4/1986 | Stuebner | 607/104 X |
| 4,738,119 | 4/1988 | Zafied | 607/104 |
| 4,747,408 | 5/1988 | Chuan-Chih | 607/104 X |
| 5,263,336 | 11/1993 | Kuramarohit | 607/104 X |

FOREIGN PATENT DOCUMENTS

2265  1/1899  United Kingdom ................ 604/291

*Primary Examiner*—Mary Beth Jones
*Attorney, Agent, or Firm*—Donald A. Bergquist

[57] ABSTRACT

A method for treating hypothermia or hyperthermia patients is presented wherein the upper torso of the patient is maintained in close contact with a wet absorbent material in a vestlike garment that carries a water supply to maintain the absorbent material wet to effect sensible heat transfer between the patient and the water. In one embodiment, evaporative cooling is moderated by an overgarment of a waterproof material.

16 Claims, 3 Drawing Sheets

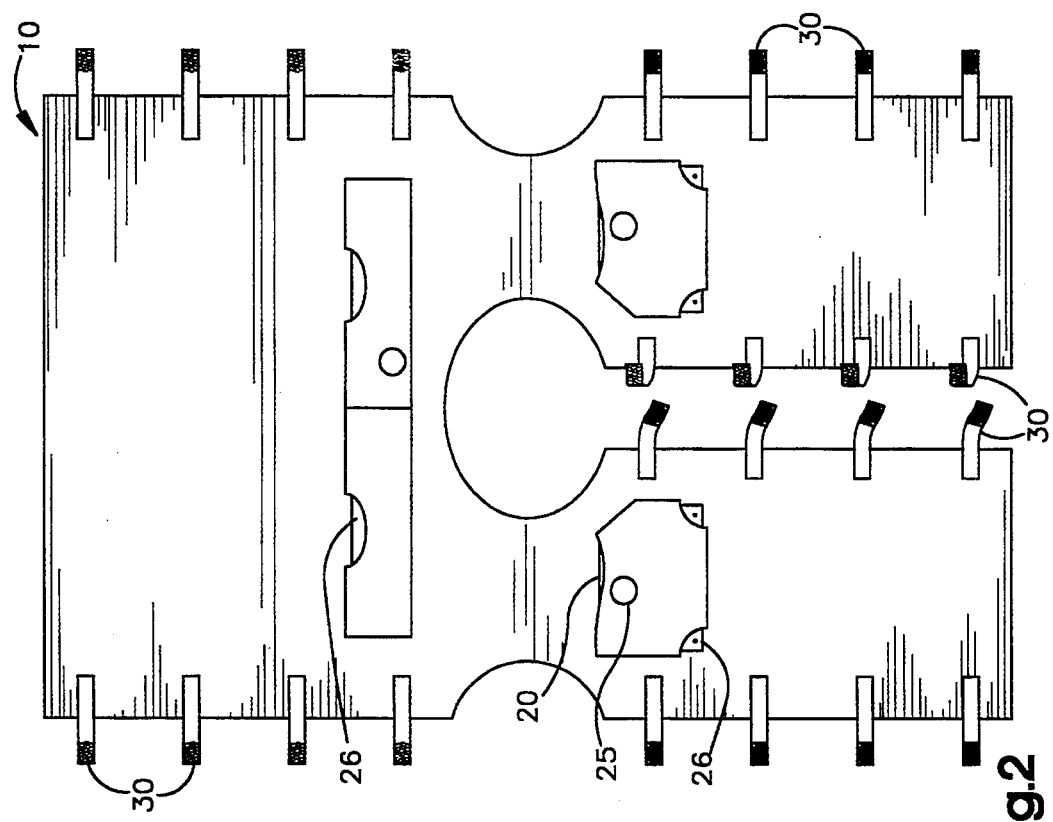
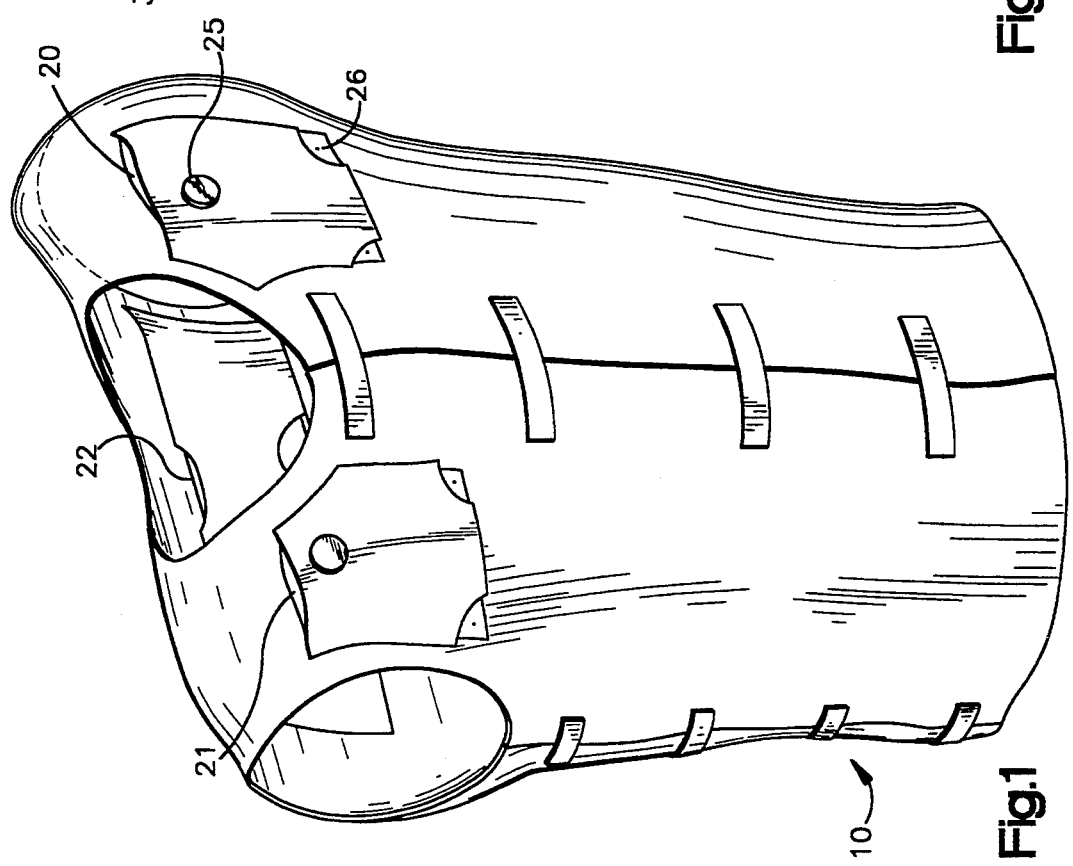

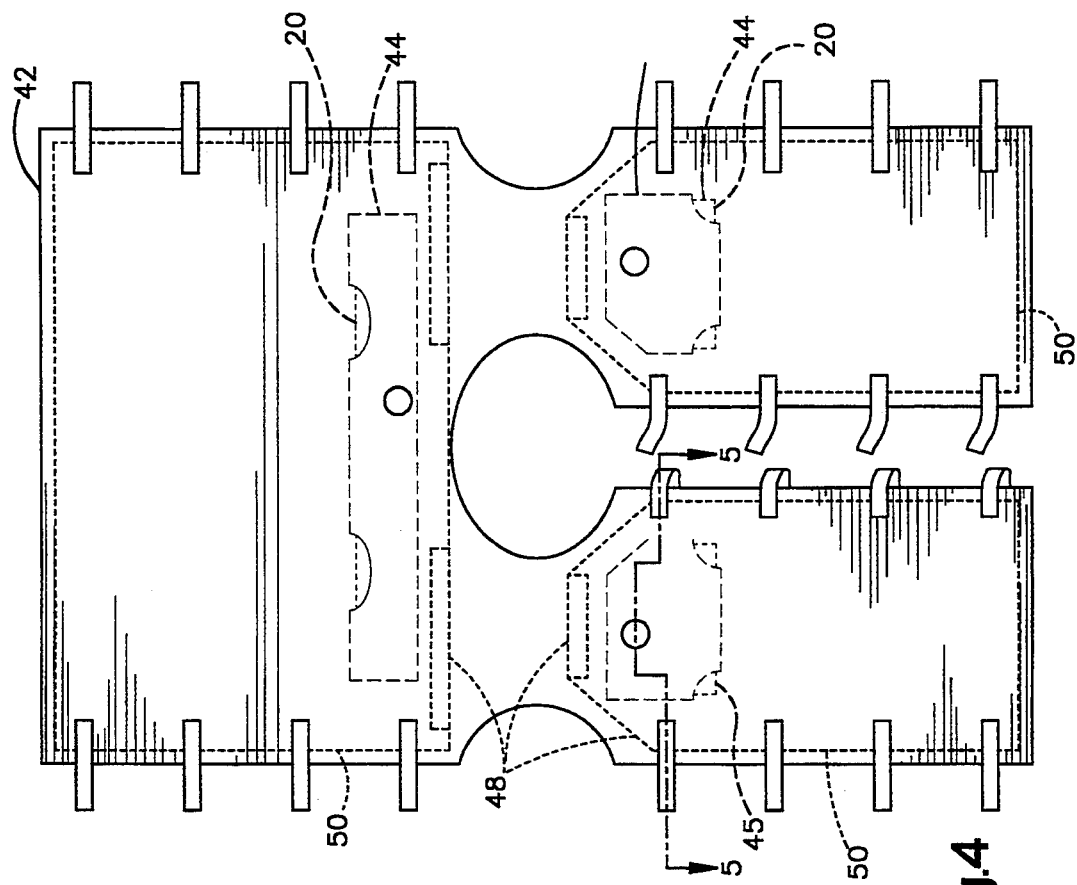
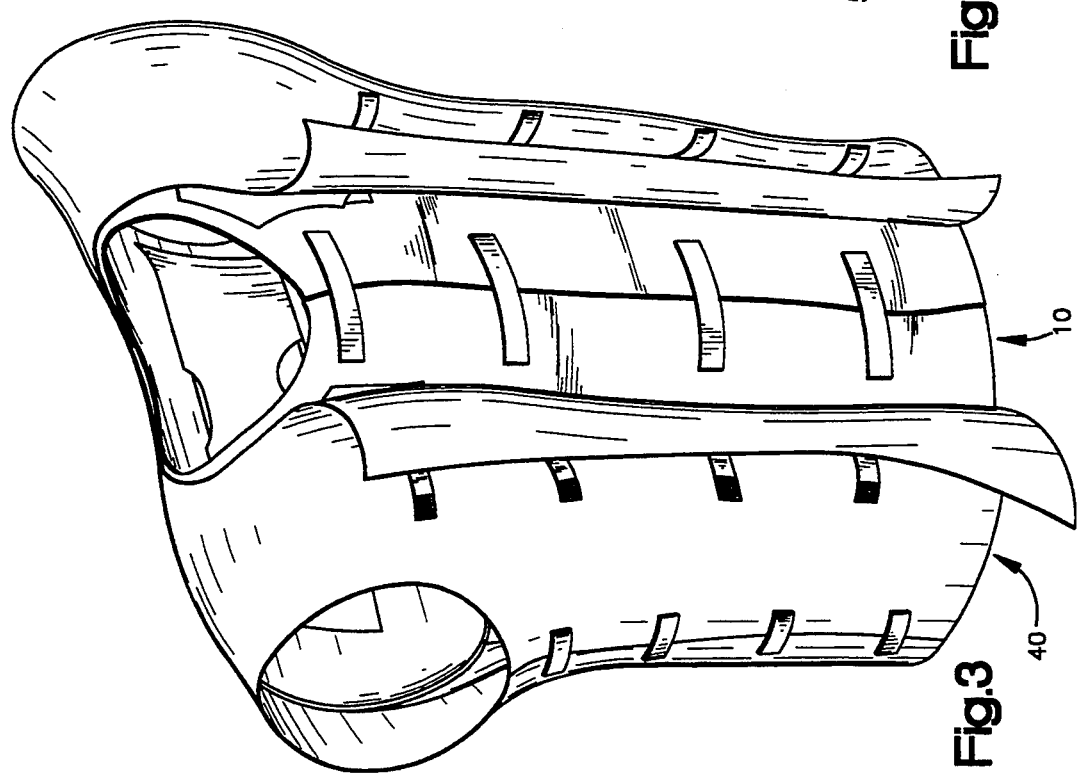

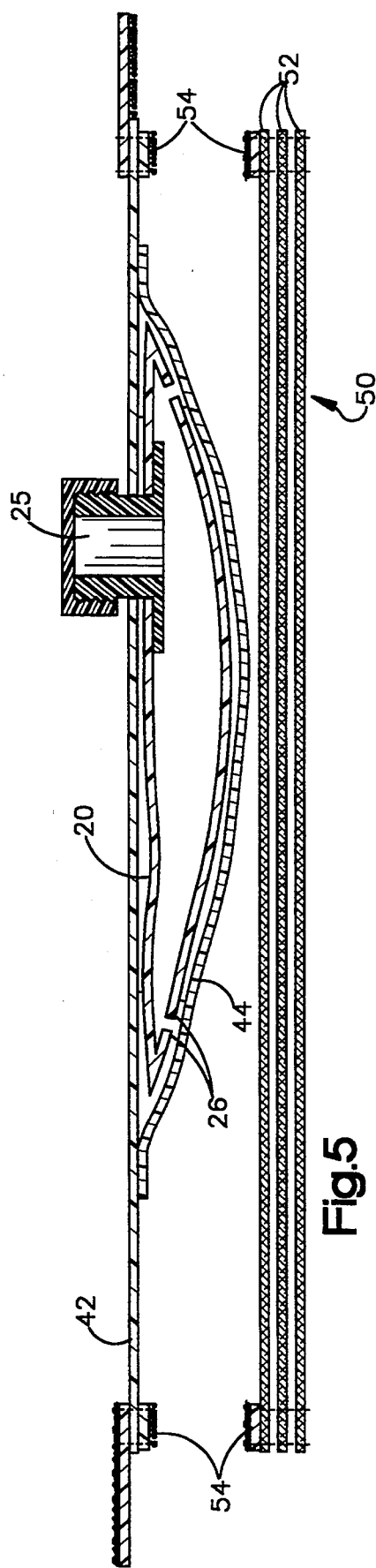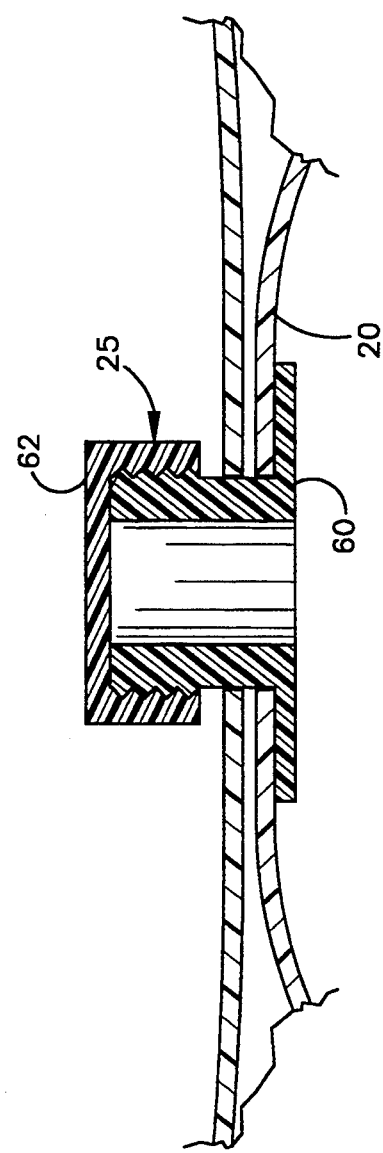

SPONGE BATH GARMENT AND METHOD FOR USING

INTRODUCTION

This disclosure relates to a method and equipment therefor to provide treatment for health care patients suffering from either acute hypothermia (excessively depressed body temperature) or acute hyperthermia (excessively elevated body temperature) by applying a specialized wetted garment to uniformly wet the torso of the patient directly with water at or near the normal temperature of the human body. The specific equipment disclosed is a vest-like garment to be worn by the patient, who may be ambulatory. The disclosure especially addresses conditions where the thermia condition (a non-standard term used here to refer to either or both hypothermia and hyperthermia) is a manifestation or symptom of an abnormal medical condition or where the thermia condition is accompanied by another abnormal medical condition. In particular it addresses the situation wherein prudent treatment of such abnormal medical condition contraindicates the use of drug therapy to achieve normal body temperature or to achieve normal body temperature without the use of drugs.

Background

At the outset, one should appreciate that, even in the health care field, where clarity may be crucial, confusion may exist in terminology in cases where similar words are used to refer to opposite conditions and or treatments. Whether this is due to a lack of knowledge, to carelessness, or to a different intent in meaning is immaterial. For our purposes, we shall adhere to the following, which we believe to be standard nomenclature. Hypothermia is a condition of depressed or subnormal body temperature; hypothermia may be treated by using medication or it may be treated by exposing the patient to a hyperthermic (warmer than normal body temperature) environment. Some might refer to the latter treatment as hyperthermia, but we caution to avoid this usage. Hyperthermia is a condition of elevated body temperature; hyperthermia may be treated by using medication or it may be treated by exposing the patient to a hypothermic (cooler than normal body temperature) environment. Some might refer to the latter treatment as hypothermia, but we caution also to avoid this usage.

The use of external cooling means to treat patients with fever (or hyperthermia) is not new. U.S. Pat. No. 1,004,192, issued in 1911 to J. T. Phelan, teaches a cooling apparatus comprising a coolant-filled cooling pipe with closed ends connected to an elevated receptacle for liquid coolant and ice. The pipe is placed adjacent to the body and especially underneath the neck and surrounding the head of the supine patient. As the coolant in the pipes becomes warm, it will be replaced by cold coolant. In contrast to the present invention, Phelan makes no suggestion that the liquid is not fully contained within the apparatus, nor can the patient using Phelan's invention be mobile.

Along a similar vein, F. C. Moore et al, in U.S. Pat. No. 3,867,939, issued in 1975, teaches a temperature-controlled applicator pad. A circuit of passages within this pad allows a thermal fluid to circulate into the pad, through a serpentine pattern of passages, and out of the pad in a forced circulation. Although the pad may be wetted, preferably with a sterile solution, to improve the heat transfer characteristics of the soft, absorbent, flexible covering, the thermal fluid is not the source of such wetting. In contrast to Moore, the present invention does not define a closed circuit for the flow of a thermal fluid; rather, the fluid-water—is distributed to an absorbent portion of the garment that provides greater dispersion of the water for contact with the skin of the patient over a substantial portion of the body, exceeding 30 percent thereof.

Another such device for forced circulation of a thermal fluid through a fluid-tight circuitous path is presented in U.S. Pat. No. 4,996,145, issued in 1990 to M. Kikumoto et al. Designed primarily for use on wheelchairs and primarily for cooling the body of the wheelchair occupant, it teaches a pump circulating a thermal fluid that is chilled by refrigeration.

U.S. Pat. No. 4,572,188, issued in 1986 to S. D. Augustine et al., teaches apparatus for controlling body temperature by means of a temperature-controlled gas mixture (usually air) supplied to an inflatable cover through which it circulates and which also serves as a plenum or manifold to transmit the temperature controlled gas to the body surfaces, thereby to thermally bathe the body in the gas. Because of the low volumetric heat capacity (measured in BTU/cu ft/degree F. or in Calories/liter/degree C.) of gases in general, and air in particular (about 1/3300 times that of liquid water), relatively large volumes of temperature-controlled gas are required to achieve the same effect of a quantity of water. The venting of the temperature-controlled gas in large quantity into the room in which the patient is being treated will thermally bathe the entire room and its other occupants in the temperature-controlled gas mixture. In contrast, the present invention uses water as a thermal medium; the use of water as a medium has little effect on the atmosphere in the room.

In U.S. Pat. No. 3,247,851, issued in 1966 to M. J. Seibert, an apparatus is taught for applying sustained moist heat to a human body by using an electrical heating jacket on an inverted bottle of a type commonly used for parentoral solutions, thereby to heat the liquid within, which is then applied by means of a drip line to moisten and to maintain an elevated temperature of a pad of adsorbent material. For extended moist heat treatment, unheated bottles may be connected in a series arrangement as may be commonly used for other purposes, but with the heated bottle being the final reservoir in the series.

Garments of various types have been used in the past to treat thermia patients and others who require external heating or cooling of their body. The following patents bear on this topic but all include a closed-circuit through which a fluid is passed for either heating or cooling. In these patents, no direct contact between the coolant or the heating fluid is taught. The processes all involve sensible heat transfer, but that transfer involves a contained fluid that is circulated through the garment and cooled by external equipment before returning to the garment. These patents include:

U.S. Pat. No. 3,507,321, Palma, 1970;
U.S. Pat. No. 3,714,947, Hardy, 1973;
U.S. Pat. No. 3,738,367, Hardy, 1973;
U.S. Pat. No. 4,691,762, Elkins et el., 1987;
U.S. Pat. No. 4,718,429, Smidt, 19881

In addition, U.S. Pat. No. 4,118,946, Tubin, 1978, teaches a garment, which could be a vest, containing in one extended compartment a viscous liquid heat transfer medium and the a second extended and vented compartment in close contact with the first and through which a compressed gas is continuously and controllably released to create a cooling effect wherein heat is extracted from said heat transfer medium for cooling the body over which said garment is worn. No direct physical contact is made between the heat transfer medium and the wearer, nor between the pressurized gas and the wearer. In contrast, the present invention requires the intimate physical contact between the skin of the wearer and the heat transfer medium, which is water, for sensible heat exchange directly therewith.

U.S. Pat. No. 4,738,119, Zafred, 1988, teaches a vest-like garment having a manifold and numerous porous tubes between an insulating garment lining and an insulating exterior garment wall. Liquid carbon dioxide is ejected into the manifold to deposit solid carbon dioxide in it and the porous tubes. Gradually, the solid carbon dioxide (i.e., "dry ice") sublimates to carbon dioxide gas that escapes through the porous tubes, the sublimation process absorbing heat, some of which comes from the body of the wearer of the garment. The temperature of the sublimation of carbon dioxide at atmospheric pressure is $-78.5$ degrees Celsius—thus the need for the insulating lining of the vest of the Zafred invention and the inadvisability of using such a garment on an individual who may be incapacitated and unable to react if exposed to such severely cold temperatures that could injure body tissue.

WIPO International Patent Application Number WO 91/04722, Graeme, published 1991, teaches a garment that is much the reverse of that of the present invention. The garment of this teaching has a felt exterior that is wetted by water from reservoirs variously located on the garment and a waterproof lining to keep the wearer dry. Additionally, pumps are present to return excess spent liquid to the reservoirs for re-use. Cooling is accomplished by evaporative cooling and heat must be transferred through the thickness of the waterproof lining and the thickness of the felt, as evaporation takes place substantially only at the outer surface thereof. In contrast, the present invention makes every effort to uniformly wet the torso of the patient directly with water at or near the normal temperature of the human body. Evaporative cooling is moderated in the best mode by covering the wet absorbent web material with a waterproof outer cover. The present invention can be used to treat hypothermia as well as hyperthermia.

Another vest incorporating evaporative cooling is taught in U.S. Pat. No. 4,580,408, Stuebner, 1986. This vest is designed for motorcycle riders and provides physical protection as well as evaporative cooling. A water absorbing layer provides water to an air cooling layer through which air is forced by the rapid motion of the wearer through the ambient air. The effect is evaporative cooling of the wearer. The water absorbing layer acts as a reservoir and is placed next to the skin. Heat passes from the wearer to the water in the absorbing layer, through to the air permeable layer where it is removed by evaporative cooling. This is also a case where more heat may be coming from the ambient air than is coming from the wearer, as the sport is often engaged in under temperature conditions in the 85- to 100-degree F. range. In contrast to the teachings of Stuebner, the present invention relies on sensible heat transfer and evaporative cooling is substantially moderated by the use of the waterproof outer covering of the best mode. In further contrast, the present invention can be used to treat hypothermia as well as hyperthermia.

U.S. Pat. No. 3,125,865, Bemelman, 1964, teaches a blouse-like water-permeable garment having a coolant reservoir at the neck to which are attached a plurality of water-permeable fibers affixed to the cloth of the garment by water-impermeable glue means, thereby to distribute water uniformly over the exterior of the garment for evaporative cooling thereof without wetting the fabric of the garment. The teachings are quite clear on the fact that the fabric of the garment be not wetted and be exposed between the strips of adhered water-permeable fibers and that the glue means be of a material that conducts heat well. In contrast, the present invention thoroughly wets the skin of the wearer, thereby to better conduct heat away from the skin. Evaporative cooling is moderated in the best mode of the present invention by a water-impermeable outer fabric shell.

U.S. Pat. No. 4,747,408, Chuan-Chih, teaches a full-body suit wherein the wearer is alternatively bathed by hot air or cooling water, thereby to simulate the effects of a sauna. A sauna is not considered a therapeutic treatment for either hypothermia nor hyperthermia; it would certainly aggravate the latter. The wearer of the Chuan-Chih garment would be connected by a cooling water supply line, electrical lines, and, most likely, a drain line, therefore he sacrifices any mobility in contrast to the wearer of the garment of the present invention.

SUMMARY OF THE INVENTION

The present invention will be seen as different from the prior art discussed above. The present invention relates to treatment of either hypothermia or hyperthermia using much the same method for each.

Applicant is not so naive as to believe that treating fever cases by administering a simple sponge bath with tepid water or even with alcohol or alcohol-water mixtures is new or novel medicine. One must realize, however, that administering such treatment is labor intensive. It is desirable, therefore, to provide a method and equipment therefor that offers effective treatment for a thermia condition without the constant presence of an attending nurse or aide.

The efficacy of this treatment has been tested, at least on a small scale. In a hospital that admitted 51 patients with simple pneumonia (including fever—i.e., hyperthermia) during the six-month period from July 1992 through December 1992, the average hospital stay for patients who were treated using conventional antipyretic drug therapy for fever (in addition to the usual intravenous fluids, oral fluids, and antibiotics) was $6\frac{1}{3}$ days ($n=48$; $s=2.74$). Three of the simple pneumonia patients were treated with a modified form of the present invention (in addition to the usual intravenous fluids, oral fluids, and antibiotics) and their average hospital stay was 3 days ($n=3$; $s=1.00$). Applying a statistical test of significance (the t-test) reveals that there is a 97-percent probability that the samples are representative of two distinct populations. That is to say, there is a 97-percent certainty that the tested treatment had an effect on the length of hospital stay. There may be bias in this result in that the doctor treating the three patients, he who decides upon whether the patient in the test sample ($n=3$) can be discharged from the hospital, is also the inventor, but the reported study is only a preliminary study to determine whether a patent should be pursued. It should not be considered as medical proof of efficacy.

Applicant believes that sponge bath therapy performs better than anti-pyretic drug therapy because, as is known, anti-pyretic drugs lower body temperature by inhibiting prostaglandins. Prostaglandins play a critical role in the immune response and other defensive mechanisms that are activated in the defense of the body against infection, so it is reasoned that inhibiting them is counterproductive to the healing process. Conventional sponge bath therapy for fever is not commonly used because it is labor intensive and is therefore used only in cases of extreme emergency.

It is an object of this invention to provide a treatment method that is therapeutically effective in treating both hypothermia and hyperthermia and comprising delivering and distributing to a large portion (at least 30%) of the surface of the body of a thermia patient a controlled flow of water at a temperature at or near that of the normal human body.

It is an object of this invention to provide apparatus for a treatment method that is therapeutically effective in treating both hypothermia and hyperthermia, which apparatus comprises equipment in the form of a vest-like garment for delivering and distributing to a large portion (at least 30%) of the surface of the body of a thermia patient a controlled flow of water at a temperature at or near that of the normal human body.

It is a further object of this invention to provide such apparatus comprising a water supply capable of delivering a water flow, an absorbent web that distributes said water flow throughout the extent thereof and thereby to an extensive area of the surface of the body of said patient over which said web is worn in vest-like fashion, thereby to make good thermal contact between said water and said patient.

It is a further object of this invention to provide such apparatus comprising a water-resistent vest-like garment under which said absorbent web is worn, thereby to moderate evaporative cooling of the absorbent web and with it the patient.

It is a further object of this invention to provide such apparatus comprising a water-resistent vest-like garment to which said absorbent web is attached to the inside thereof.

It is yet another object of this invention to provide a specific embodiment of the apparatus wherein said water source is a refillable reservoir that is worn near the shoulders of the patient, thereby to provide for water flow therefrom by the action of gravity alone.

It is yet another object of this invention to provide a specific embodiment of the apparatus wherein said water source is a plurality of refillable reservoirs.

It is yet another object of this invention to provide a specific embodiment of the apparatus wherein said water source is carried in pockets in said web.

It is yet another object of this invention to provide a specific embodiment of the apparatus wherein said water source is carried in pockets in said water-resistant garment.

These, and other objects of this invention, will become abundantly clear to the reader in the following detailed description of the invention.

BRIEF DESCRIPTION OF THE DRAWINGS

FIG. 1 illustrates a vest-like garment of the present invention made of an absorbent material.

FIG. 2 illustrates the plan for the garment shown in FIG. 1.

FIG. 3 illustrates the garment of FIG. 1 with an overgarment that prevents evaporative cooling.

FIG. 4 illustrates the plan for a preferred mode wherein absorbent panels attach to an overgarment.

FIG. 5 illustrates a cross-section view of the article shown in FIG. 4 taken along the line 5—5.

FIG. 6 illustrates a cross-section view of details from FIG. 5.

DETAILED DESCRIPTION OF THE INVENTION

This invention will be most easily understood by referring to the attached drawings, wherein parts are identified by reference numbers consistent with the following description. In each view, the same part carries the same reference number.

In the process of this invention, an ambulatory or non-ambulatory thermia patient is fitted with a size-adjustable vest-like garment having an absorbent layer to be placed against and covering at least 30 percent of the skin of the thermia patient. The absorbent layer and the underlying skin of the thermia patient is to be kept moist with water at or near the normal temperature of the human body. Neither cold water nor hot water should be used. Although evaporation from the absorbent layer is best minimized by reducing air currents about the layer, some evaporation is bound to occur, so additional water at or near body temperature must be added to the absorbent layer. The heat transfer between the patient and the water held by the absorbent layer ameliorates the thermia condition.

Suitable equipment for practicing the process of this invention is illustrated in FIG. 1, which shows a vest-like garment 10 made of an absorbent material and having one or more refillable water reservoirs 20 21 22 mounted about the yoke of the garment. Each reservoir has a filler opening 25 with a substantially water-tight cap, details of which will be later proffered. Each reservoir also has a weep hole 26 near a portion thereof that is lowest when the garment is worn. As the garment is worn, water will slowly flow from the weep hole and onto a portion of the absorbent material to replenish any water lost by evaporation from the absorbent layer. The material of the absorbent layer is selected to have excellent wicking properties, thereby to readily receive the water flow and to distribute it over the area of the absorbent layer. For the simple garment illustrated in FIG. 1, 100-percent cotton terrycloth is preferred for the absorbent material.

A suitable garment 10 for use as shown in FIG. 1 can be easily manufactured from a single flat piece of absorbent material. The plan for such a garment is shown in FIG. 2. The adjustable fastening tabs 30 illustrated in FIG. 1 and in subsequent figures utilize hook-and-loop materials, typically referred to by the brand name VELCRO.

The garment of FIGS. 1 and 2 is intended to be worn in an environment wherein evaporative heat loss from the wetted garment is moderated. This would be true in a humid atmosphere with little or no draft.

An overgarment 40, as shown in FIG. 3, would be desirable in most environments, especially where mechanical or natural forces circulate the air effectively. The overgarment must be of a non-absorbent material that would also prevent drafts from reaching the wetted absorbent material. For use on a patient who is in bed, whether seated, reclining, or supine, a waterproof overgarment is required to prevent soaking the bed linens while reducing evaporative heat loss, although a waterproof underlay merit could do the former, but not the latter.

A preferred embodiment combines the concepts of the overgarment and the absorbent material of the previously-described absorbent garment. One such example of the preferred embodiment is shown laid out in plan form in FIG. 4. This example provides an overgarment 42 with pockets 44 for holding warm water reservoirs 20 and means 48 for attaching absorbent panels 50 on the inside thereof. It is preferred that the overgarment be made from a waterproof fabric. In practice, a woven nylon fabric that is coated with butyl rubber on both the inside and the outside surfaces has been found suitable and has been used in a working model, although the search for more economical materials is continuing.

FIG. 4 shows the location of the several water reservoirs 20 in pockets on both the front and the back of the garment. Each pocket has a cutout 45 at the bottom thereof to allow the reservoir to be exposed to the absorbent panels that attach to the inside of the overgarment. Each reservoir has a weep hole 26 through the wall thereof in the area exposed by the pocket cutouts. Tests have shown that the placement of the reservoir on the back yoke of the garment places it high enough on the back: of the patient that it does not interfere with the comfort of a typical reclining patient.

The absorbent panels 50 are attached at multiple points 48 to the inside of the overgarment 42. In practice, the use of hook-and-loop fabric tabs (i.e., VELCRO) has been suitable. One might use buttons, metal or plastic snaps, or other means for attaching the absorbent panels with equal success.

In practice, the absorbent panels for use in the overgarment of FIG. 4 have been cut from 100-percent cotton terrycloth. Samples were also made up as shown in FIG. 5, using panels comprising multiple layers of paper toweling and was found totally suitable for disposable absorbent panels. For this use, paper toweling of a particular brand was found especially well suited because of its strength when wet, its high absorbancy, and its excellent wicking characteristics; that brand is BOUNTY, made by Procter & Gamble Co., of Cincinnati, Ohio, incorporated in the state of Ohio. In such a configuration, the absorbent panels may be disposable while the overgarment may be laundered, sterilized (if need be), and re-used.

In FIG. 5, one can see that multiple layers 52 of absorbent material makes up the absorbent panels 50, of which one example is shown. The absorbent panel attaches to the inside of the overgarment 42 by means of VELCRO tabs 54. The water reservoir 20 is held within the pocket 44. The filler opening 25 of each reservoir extends through an opening in the overgarment to provide for easy access for filling and refilling the reservoir. The reservoir found most suitable is a baglike thin walled flexible thermoplastic bladder with a screw-capped filler opening. Each reservoir also has a weephole 26 to permit water flow from the reservoir and onto the absorbent panel. In the best mode, the flexible walls of the reservoir collapse as the water drains from the reservoir, thus obviating any means for venting air into the reservoir and making the weephole the only egress for the water after the filler opening is capped.

FIG. 6 illustrates in detail the joining of the filler opening to the reservoir and further illustrates how the filler opening of the best mode projects through the wall of the garment to allow filling while the garment is being worn. In this drawing, a wall of of the reservoir 20 has a hole through it into which a screw-cap fitting 60 is placed and permanently affixed. As the reservoir is placed in the retaining pocket, the screw-cap fitting may then be inserted through a matching opening in the fabric of the garment 42 from the inside to the outside to present the filler opening on the exterior of the garment. The filler opening is then capped with a removable cap, a screw cap 62 being shown in the drawing.

It should be considered a natural extension of this disclosure to produce a vest-like garment of totally disposable materials, such as the paper of which BOUNTY paper towels are made, with or without a waterproof outer covering, and having one or more water reservoirs associated therewith. It is believed that such a garment falls within the claims appended hereto.

I claim:

1. A therapeutic treatment method for use in treating a thermia condition in a human patient by providing sensible heat transfer between the patient and water at a temperature of substantially that of the normal human body while allowing near total mobility of the patient, said method comprising providing a vest-like garment comprising an absorbent material maintained substantially in contact with the skin of the upper torso of the thermia patient, and providing water at a temperature of substantially that of the normal human body, said water to be temporarily retained in a water reservoir carried by said garment while it is worn by said patient, said reservoir having a weephole from which said water escapes from said reservoir by hydrostatic pressure under the force of gravity onto said absorbent material, thereby to maintain said absorbent material and the underlying skin of the thermia patient in a wet condition and at a temperature approximating that of the normal human body and to thereby effect sensible heat transfer between said water and said human patient, thereby to ameliorate said thermia condition.

2. A therapeutic treatment method according to the teachings of claim 1 with the added step of providing an overgarment covering said absorbent material, thereby to substantially moderate evaporative cooling of said wetted absorbent material.

3. A therapeutic treatment method according to the teachings of claim 1 wherein said thermia condition is hypothermia.

4. A therapeutic treatment method according to the teachings of claim 1 wherein said thermia condition is hyperthermia.

5. Apparatus for a therapeutic treatment method for use in treating a thermia condition in a human patient, which apparatus comprises:

a vest-like garment comprising an absorbent material maintained in substantial contact with the skin of the upper torso of the thermia patient when said garment is worn, said absorbent material contacting at least thirty percent of the total area of skin of said patient;

a reservoir having a lower end, said reservoir holding water at a temperature of substantially that of the normal human body, means to support said reservoir by said garment, whereby said reservoir is carried by said patient while said garment is worn, allowing mobility of said patient;

an outlet substantially at said lower end of said reservoir through which substantially all said water may leak from said reservoir and onto said absorbent material under hydrostatic pressure and the force of gravity, thereby to maintain said absorbent material and the immediately underlying skin of said thermia patient in a wet condition and with said water at a temperature approximating that of the normal human body and to thereby effect sensible heat transfer between said water and said human patient, thereby to ameliorate said thermia condition.

6. The apparatus of claim 5 wherein said reservoir is a baglike container having a wall and also having a filling opening with a removable sealable cap, said wall having said outlet in the form of a weephole therethrough, through which weephole water contained within said reservoir can exit.

7. The apparatus of claim 5 wherein said reservoir support means comprises a pocket in said garment and wherein said pocket can securely support said reservoir and wherein said pocket is in a region of said garment proximal a neck opening and an arm opening therein.

8. The apparatus of claim 5 wherein said absorbent material is a cotton terrycloth fabric.

9. The apparatus of claim 5 wherein said absorbent material is an absorbent paper product.

10. Apparatus for a therapeutic treatment method for use in treating a thermia condition in a human patient, which apparatus comprises:
a vest-like garment comprising a waterproof fabric having a lining comprising an absorbent material that is, by virtue of its lining the waterproof fabric, is maintained in substantial contact with the skin of the upper torso of the thermia patient when said garment is worn, said absorbent material contacting at least thirty percent of the total area of skin of said patient;
a reservoir having a lower end, said reservoir holding water at a temperature of substantially that of the normal human body, means to support said reservoir by said waterproof garment, whereby said reservoir is carried by said patient while said garment is worn, allowing mobility of said patient; and
an outlet substantially at said lower end of said reservoir through which substantially cell said water may leak from said reservoir and onto said absorbent material under hydrostatic pressure and the force of gravity;
thereby to maintain said absorbent material and the immediately underlying skin of said thermia patient in a wet condition and with said water at a temperature approximating that of the normal human body and to thereby effect sensible heat transfer between said water and said human patient, thereby to ameliorate said thermia condition.

11. The therapeutic apparatus of claim 10 wherein said waterproof fabric is woven nylon coated with butyl rubber.

12. The therapeutic apparatus of claim 10 wherein said absorbent material is terrycloth.

13. The therapeutic apparatus of claim 12 wherein said terrycloth is substantially one-hundred percent cotton.

14. The therapeutic apparatus of claim 10 wherein said absorbent material is absorbent paper.

15. The therapeutic apparatus of claim 10 wherein said absorbent material is removably attached to said waterproof fabric.

16. The therapeutic apparatus of claim 15 wherein said absorbent material is attached by means of hook-and-loop fastenings.

* * * * *